United States Patent
Zhai et al.

(10) Patent No.: US 11,536,623 B2
(45) Date of Patent: Dec. 27, 2022

(54) DIGITAL PRESSURE SENSOR WITH RUBBER COVER

(71) Applicants: Measurement Specialties (China) Ltd., Shenzhen (CN); Measurement Specialties, Inc., Hampton, VA (US)

(72) Inventors: Yang Zhai, Shenzhen (CN); Xu Liang, Shenzhen (CN); Jianjie Yuan, Shenzhen (CN); John Valentini, Fremont, CA (US); Bala Kashi, Fremont, CA (US)

(73) Assignees: Measurement Specialties (China) Ltd., Shenzhen (CN); Measurement Specialties, Inc., Hampton, VA (US)

( * ) Notice: Subject to any disclaimer, the term of this patent is extended or adjusted under 35 U.S.C. 154(b) by 153 days.

(21) Appl. No.: 17/085,438

(22) Filed: Oct. 30, 2020

(65) Prior Publication Data

US 2021/0131899 A1    May 6, 2021

(51) Int. Cl.
  *G01L 19/00*    (2006.01)

(52) U.S. Cl.
  CPC ...... *G01L 19/00* (2013.01); *G01L 2019/0053* (2013.01)

(58) Field of Classification Search
  CPC ... G01L 3/24; G01L 3/242; G01L 5/08; G01L 5/10; G01L 5/101; G01L 5/108; G01L 5/16; G01L 5/1627; G01L 5/167; G01L 5/22; G01L 5/28; G01L 23/085; G01L 23/20; G01L 5/0061; G01L 5/0071; G01L 5/008; G01L 5/06; G01L 5/171; G01L 7/106

USPC .................................................. 73/700–756
  See application file for complete search history.

(56) References Cited

U.S. PATENT DOCUMENTS

| | | | | |
|---|---|---|---|---|
| 3,762,223 | A * | 10/1973 | Feuer | G01L 9/0016 73/702 |
| 4,625,560 | A * | 12/1986 | Sanders | G01L 15/00 331/65 |
| 4,644,482 | A * | 2/1987 | Juanarena | G01L 9/0008 73/579 |
| 11,125,627 | B2 * | 9/2021 | Jenkner | G01K 7/01 |
| 2002/0117006 | A1 * | 8/2002 | Paros | G01L 9/0026 73/717 |

(Continued)

FOREIGN PATENT DOCUMENTS

| | | | | |
|---|---|---|---|---|
| CN | 113218569 A * | 8/2021 | | |
| WO | WO-2015004635 A2 * | 1/2015 | ........ | G01L 19/0084 |
| WO | WO-2019175537 A1 * | 9/2019 | ............ | F17C 13/025 |

*Primary Examiner* — Andre J Allen
(74) *Attorney, Agent, or Firm* — Barley Snyder (57) ABSTRACT

A digital pressure sensor includes a substrate, a pressure sensing structure configured for measuring a pressure of an object to be measured, a signal processing chip configured for receiving a sensing signal of the pressure sensing structure, and a rubber cover having an opening through which the pressure is sensed. The pressure sensing structure and the signal processing chip are mounted on the substrate. The signal processing chip has an analog-digital conversion module that converts the sensing signal output by the pressure sensing structure into a digital signal and outputs the digital signal. The signal processing chip is electrically connected to the substrate. The substrate and the rubber cover are connected to each other and form a mounting cavity for holding the pressure sensing structure and the signal processing chip.

16 Claims, 5 Drawing Sheets

(56) References Cited

U.S. PATENT DOCUMENTS

| | | | | |
|---|---|---|---|---|
| 2010/0139411 A1* | 6/2010 | Wu | ............... | G01L 19/16 |
| | | | | 73/756 |
| 2013/0218501 A1* | 8/2013 | Artiuch | ............ | G01L 27/005 |
| | | | | 702/98 |
| 2013/0218502 A1* | 8/2013 | Artiuch | ............ | G01L 27/005 |
| | | | | 702/98 |
| 2021/0369126 A1* | 12/2021 | Khachaturian | .... | A61B 5/02225 |

\* cited by examiner

DIGITAL PRESSURE SENSOR WITH RUBBER COVER

CROSS-REFERENCE TO RELATED APPLICATION

This application claims the benefit of the filing date under 35 U.S.C. § 119(a)-(d) of Chinese Patent Application No. 201921851206.X, filed on Oct. 31, 2019.

FIELD OF THE INVENTION

The present invention relates to a sensor and, more particularly, to a digital pressure sensor.

BACKGROUND

Medical pressure sensors are widely used in surgery because of its real-time testing of variation in a patient's blood pressure. The medical pressure sensor is to puncture the needle tube into the blood vessel of the object to be detected with the outer end of the needle tube being directly connected to the pressure sensor. Since fluid can transfer pressure, the pressure in the blood vessel is transferred to the external pressure sensor through the liquid in the catheter so as to obtain the dynamic waveform of real-time pressure variations in the blood vessel.

Current medical pressure sensors often output dynamic waveforms of pressure variations to an external display device in the form of electrical signals, which is not conducive for the operator to know the blood pressure of the detected object in real time, and the operation is extremely inconvenient. In addition, in the existing medical pressure sensors, a screen-printed thick film resistor is often welded to the substrate after being cut by laser to compensate for the bridge resistance on the main orifice plate and balance the bridge, which is not conducive to production and manufacturing of the medical pressure sensor.

SUMMARY

A digital pressure sensor includes a substrate, a pressure sensing structure configured for measuring a pressure of an object to be measured, a signal processing chip configured for receiving a sensing signal of the pressure sensing structure, and a rubber cover having an opening through which the pressure is sensed. The pressure sensing structure and the signal processing chip are mounted on the substrate. The signal processing chip has an analog-digital conversion module that converts the sensing signal output by the pressure sensing structure into a digital signal and outputs the digital signal. The signal processing chip is electrically connected to the substrate. The substrate and the rubber cover are connected to each other and form a mounting cavity for holding the pressure sensing structure and the signal processing chip.

BRIEF DESCRIPTION OF THE DRAWINGS

The invention will now be described by way of example with reference to the accompanying Figures, of which.

DETAILED DESCRIPTION OF THE EMBODIMENTS

In order to make the technical problem to be solved by the present disclosure, technical solution, and advantageous effect clearer, the present disclosure is elaborated with reference to the drawings and embodiments as follows. It should be understood that the embodiments described here are only used to explain the present disclosure and do not limit the present disclosure. Further, the drawings in the following description are only some of the embodiments of the present disclosure; for those skilled in the art, it does not require any creative labor to obtain other drawings based on these drawings.

It should be noted that an element may be directly on another element or indirectly on the another element when referred to as being "fixed to" or "provided on" another element. An element may be directly connected to another element or indirectly connected to the another element when referred to as being "connected to" another element. In the description of the present disclosure, it should be noted that, unless otherwise clearly provided and defined, the terms "mounting", "connect" and "connection" should be understood in a broad sense. For example, it may be fixed connection or detachable connection, or integrated connection; it may be mechanical connection or electrical connection; it may be direct connection, or indirect connection through an intermediate medium, and it may be the internal communication between two elements or the interaction between two elements. Those skilled in the art can understand the specific meaning of the above terms in the present disclosure according to specific situations.

Figure 1:
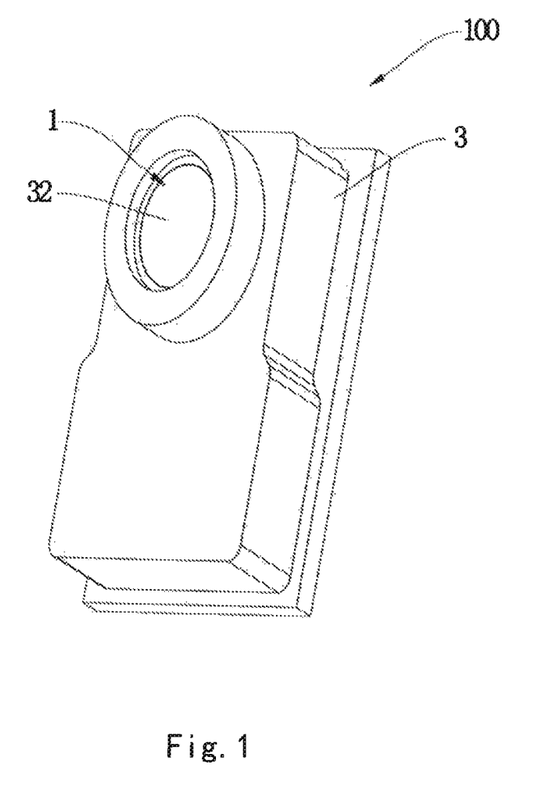
FIG. 1 is a perspective view of a digital pressure sensor according to an embodiment.
Figure 2:
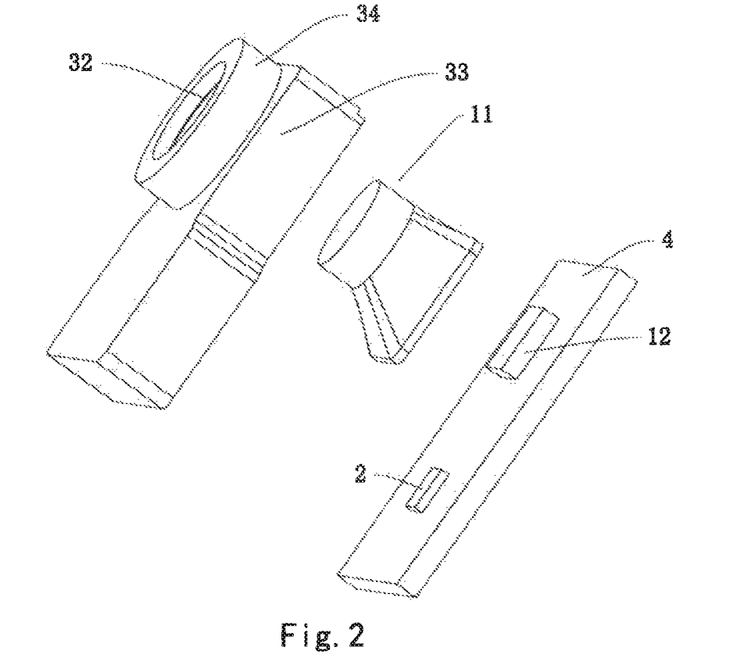
FIG. 2 is an exploded perspective view of the digital pressure sensor of FIG. 1.

A digital pressure sensor 100 according to an embodiment is shown in FIGS. 1 and 2. The digital pressure sensor 100 includes a pressure sensing structure 1, a signal processing chip 2, a rubber cover 3, and a substrate 4. The pressure sensing structure 1 is used to detect the pressure of the object to be measured, such as detecting the blood pressure of the object to be measured, and the pressure of the effusion inside a female patient's uterus, etc. The signal processing chip 2 is used to receive the sensing signal of the pressure sensing structure 1. The pressure sensing structure 1 and the signal processing chip 2 are mounted on the substrate 4 respectively, and the substrate 4 and the rubber cover 3 are connected to each other.

Figure 3:
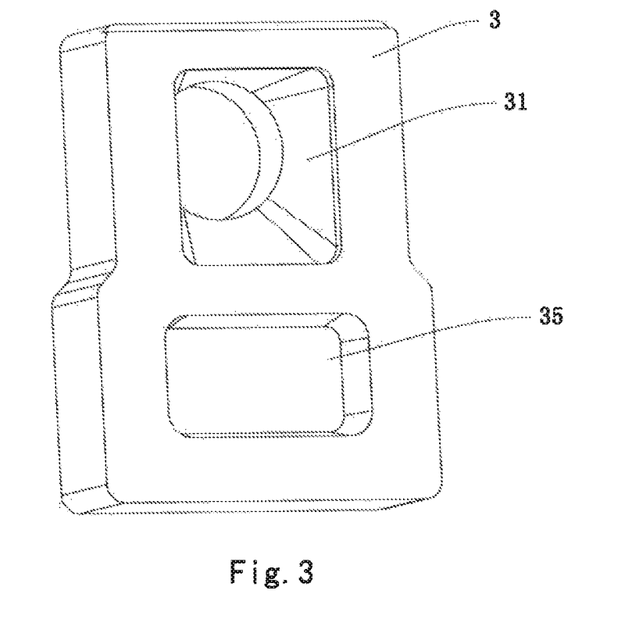
FIG. 3 is a perspective view of a rubber cover of the digital pressure sensor of FIG. 1.

The rubber cover 3, as shown in FIGS. 1-3, is provided with a mounting cavity 31. The substrate 4 is covered by a port of the mounting cavity 31 such that the pressure sensing structure 1 and the signal processing chip 2 are arranged into the mounting cavity 31 such that the pressure sensing structure 1 and the signal processing chip 2 are secured within the mounting cavity 31. The rubber cover 3 has an opening 32 for sensing pressure, and the pressure is transferred to the pressure sensing structure 1 through the opening 32.

Figure 4:
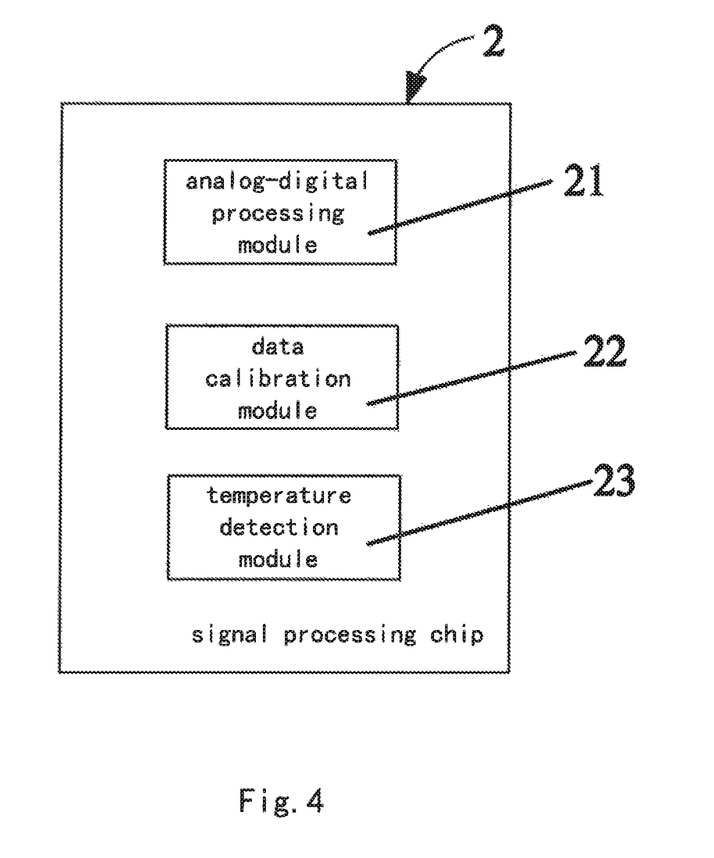
FIG. 4 is a schematic diagram of a substrate of the digital pressure sensor of FIG. 1.

The signal processing chip 2 includes an analog-digital conversion module 21, as shown in FIG. 4. The signal processing chip 2 is electrically connected to the substrate 4, as shown in FIGS. 1 and 2. The analog-digital conversion module 21 may convert the sensing signal output by the pressure sensing structure 1 into a digital signal, and output the digital signal to an external display device, so as to make it easy for the operator to understand the pressure data of the object to be measured in real time.

In an embodiment, the digital pressure sensor 100 may be used to measure blood pressure of a human body. A housing is needed to support the digital pressure sensor 100 during the measuring of human blood pressure. A through hole is provided in the middle of the housing and the housing is provided with a mounting groove on the side wall of the through hole. The digital pressure sensor 100 is mounted in the mounting groove such that the opening 32 of the rubber cover 3 faces the through hole. The hose connected to the patient's blood vessel passes through the through hole such that the opening 32 of the rubber cover 3 extends into the hose so that the pressure sensing structure 1 can measure the blood pressure of the human body. The sensing signal is transmitted to the signal processing chip 2. The signal processing chip 2 converts the sensing signal into a digital signal and outputs it to an external display device so that the doctor can obtain the patient's blood pressure index in real time, which is conducive for the doctor to respond in time when the patient's blood pressure is unstable. For example, the patient's arterial blood pressure changes drastically in a short period of time, which may even lead to cardiovascular complications and increase mortality. The digital pressure sensor 100 is used to monitor the patient's blood pressure at any time, thereby effectively avoiding the occurrence of such situations and reducing the risk of accidents for patients.

In the embodiment shown in FIGS. 1-3, the pressure sensing structure 1 includes a soft rubber 11 and a pressure sensing chip 12. The pressure sensing chip 12 is provided on one side of the soft rubber 11 away from the opening 32 of the rubber cover 3. The pressure sensing chip 12 is electrically connected to the substrate 4 so that pressure is applied to the soft rubber 11 through the opening 32 on the rubber cover 3. The soft rubber 11 deforms under pressure and transfers the pressure to the pressure sensing chip 12. The pressure sensing chip 12 senses the deformation of the soft rubber 11 and generates a sensing signal, and then outputs the sensing signal to the signal processing chip 2, where the sensing signal is an electrical signal. The signal processing chip 2 may obtain a digital signal by processing the sensing signal after receiving it and output the digital signal to an external display device, so as to make it easy for the operator to obtain the measured pressure data in real time.

In the embodiment shown in FIGS. 1 and 2, the soft rubber 11 is silica gel with which the mounting cavity 31 is filled. Silica gel has good flexibility such that the soft rubber 11 may deform greatly under pressure, which is advantageous for the pressure sensing chip 12 to sense the deformation of the soft rubber 11. In addition, the digital pressure sensor 100 can be used to measure the pressure of liquids such as the patient's body fluids or blood. The mounting cavity 31 of the rubber cover 3 is provided with soft rubber 11 to prevent the pressure sensor chip 12 from directly contacting the liquid, thereby protecting the pressure sensing chip 12.

As shown in the embodiment of FIG. 4, the signal processing chip 2 further includes a temperature detection module 23 capable of sensing the temperature of the signal processing chip 12, thereby obtaining the body temperature value of the detected object in real time. Specifically, the temperature detection module 23 is electrically connected to the pressure sensing structure 1 such that the temperature detection module 23 may indirectly know the temperature value of the detected object by detecting the temperature variation of the pressure sensing structure 1, and the temperature value is displayed through an external display device, which is conducive to monitoring the body temperature of the detected object at any time. This structure can not only monitor the pressure value of the patient, but also obtain the temperature value of the patient in time, detecting the patient's physical signs from multiple angles and providing a complete guarantee for the patient's health detection.

In the embodiment shown in FIGS. 1 and 2, the digital pressure sensor 100 further includes a metal wire. The metal wire may electrically connect the pressure sensing chip 12 to the signal processing chip 2 such that the sensing signal of the pressure sensing chip 12 may be transmitted to the signal processing chip 2 through the metal wire so that the signal processing chip 2 may convert the sensing signal into a digital signal that facilitates user reading.

The digital pressure sensor 100, in the embodiment of FIGS. 2-4, further includes an interaction device mounted on an outer surface of the rubber cover 3. The interaction device is electrically connected to the signal processing chip 2, wherein the interaction device can be an operation panel that includes a power-on button, a power-off button, an alarm button, and an alarm stop button, etc. . . . Correspondingly, the external display device includes an alarm module. When the digital pressure sensor 100 is used to measure the patient's blood pressure or body temperature, the operator can set the corresponding parameter alarm value to the external display device through the operation panel in advance. When the patient's blood pressure or body temperature is higher or lower than a certain set value, the alarm module will give out an alarm to notify the relevant nursing staff and doctors in time.

The rubber cover 3, as shown in the embodiment of FIGS. 1-3, includes a base 33 and a boss 34 having a ring structure and provided on the boss 33. The boss 34 is provided with a first groove, a second groove is provided at a position of the base 33 corresponding to the first groove, wherein the first and second grooves communicate with each other such that the first groove and the second groove constitute the mounting cavity 31. The pressure sensing structure 1 is mounted within the mounting cavity 31. A second cavity 35 is provided on the base 33, the second cavity 35 and the mounting cavity 31 are spaced apart; the signal processing chip 2 is placed in the second cavity 35. Two cavities 31, 35 are spaced apart on the rubber cover 3, and the signal processing chip 2 and the pressure sensing structure 1 are respectively placed in different cavities so as to prevent the pressure sensing structure 1 from directly squeezing the signal processing chip 2, thereby protecting the signal processing chip 2.

The signal processing chip 2, in an embodiment shown in FIG. 4, further includes a data calibration module 22 capable of compensating for the sensing signal on the signal processing chip 2 to reduce the measurement error of the pressure sensor chip 12, thereby improving detection accuracy, and eliminating soldering the screen printed thick film resistor on the substrate 4 to facilitate the production of the sensor.

Figure 5:
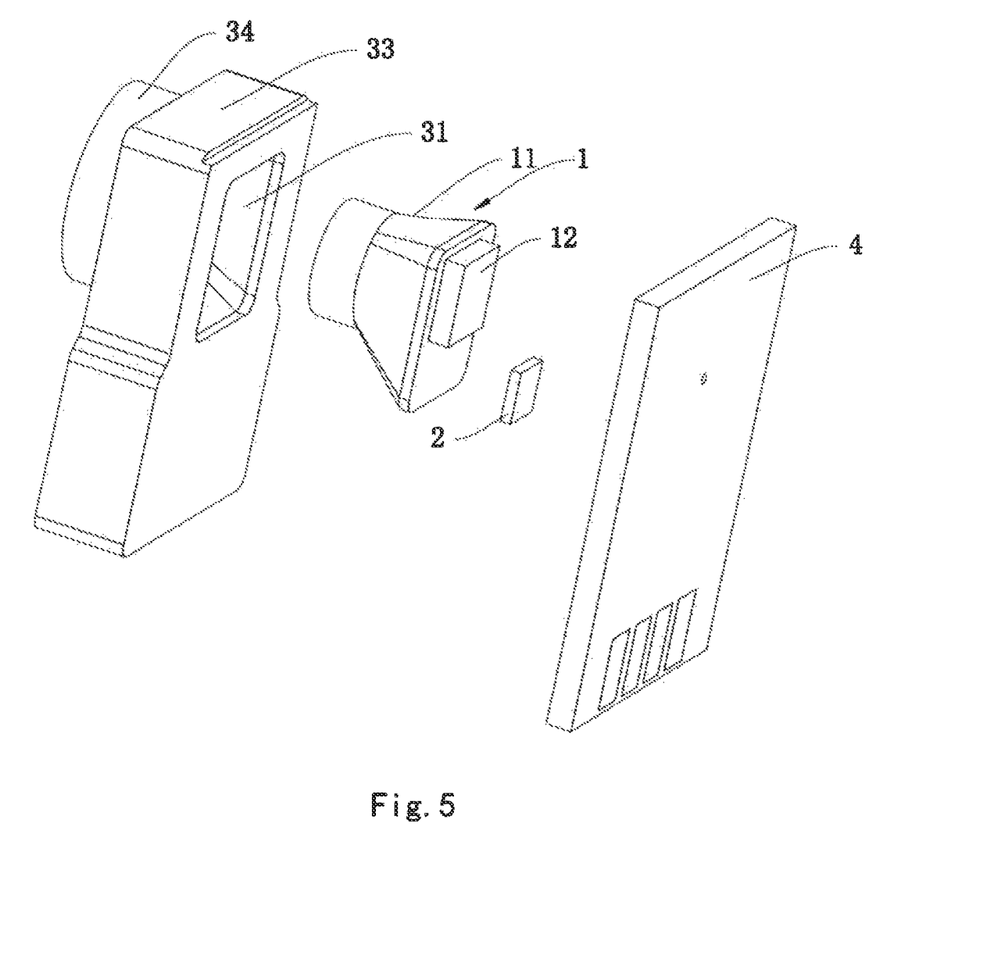
FIG. 5 is an exploded perspective view of a digital pressure sensor according to another embodiment.

A digital pressure signal 100 according to another embodiment is shown in FIG. 5; the difference between the digital pressure sensor of this embodiment and that of first embodiment lies in that the signal processing chip 2 and the pressure sensing structure 1 are placed at different positions.

The digital pressure sensor 100 in the embodiment of FIG. 5 includes a pressure sensing structure 1, a signal processing chip 2, a rubber cover 3, and a substrate 4. The pressure sensing structure 1 is used to detect the pressure of an object to be measured, such as the blood pressure of the object to be measured, and the pressure of the effusion inside a female patient's uterus, etc. . . . The signal processing chip 2 may receive the sensing signal of the pressure sensing structure 1. The pressure sensing structure 1 and the signal processing chip 2 are respectively mounted on the substrate 4, and the substrate 4 and the rubber cover 3 are connected to each other, wherein the rubber cover 3 is provided therein with a mounting cavity 31. The substrate 4 covers the port of the mounting cavity 31 so that the pressure sensing structure 1 and the signal processing chip 2 are placed in the mounting cavity 31. The rubber cover 3 is provided with an opening 32 for sensing pressure, and the pressure is transferred to the pressure sensing structure 1 through the opening 32. The signal processing chip 2 includes an analog-digital conversion module 21, and the signal processing chip 2 is electrically connected to the substrate 4.

The rubber cover 3, as shown in FIG. 5, includes a base 33 and a boss 34 having an annular structure provided on the base 33. The boss 34 is provided with a first groove, and a second groove is provided at the position of the base 33 corresponding to the first groove, wherein the first groove and the second groove communicate with each other to form a mounting cavity 31.

The pressure sensing structure 1 and the signal processing chip 2 are stacked sequentially in the mounting cavity 31 in the embodiment of FIG. 5. The signal processing chip 2 and the pressure sensing structure 1 are stacked sequentially in the mounting cavity 31 such that the signal processing chip 2 and the pressure sensing structure 1 cooperate compactly, and the length of the metal wire for connecting the signal processing chip 2 with the pressure sensing structure 1 is reduced, thereby reducing the influence of the resistance in the metal wire on the sensing signal output by the pressure sensing structure 1, thereby improving the accuracy of detection.

Figure 6:
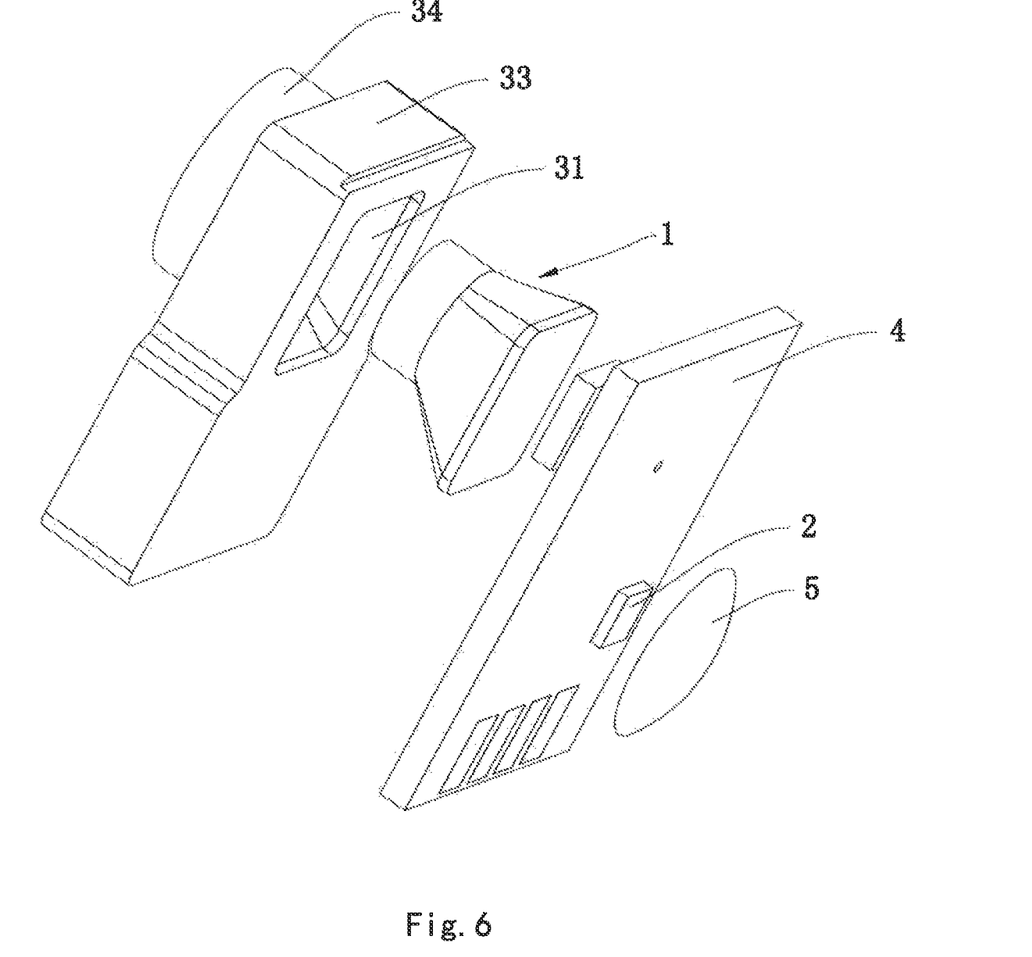
FIG. 6 is a exploded perspective view of a digital pressure sensor according to another embodiment.

A digital pressure sensor according to another embodiment is shown in FIG. 6; the difference between the digital pressure sensor of this embodiment and that of the second embodiment lies in that the signal processing chip 2 and the pressure sensing structure 1 are arranged at different positions.

The digital pressure sensor 100 in the embodiment of FIG. 6 includes a pressure sensing structure 1, a signal processing chip 2, and a rubber cover 3, and a substrate 4. The pressure sensing structure 1 is used to detect the pressure of the object to be measured, such as the blood pressure of the object to be measured, and the pressure of the effusion inside a female patient's uterus, etc. . . . The signal processing chip 2 may receive the sensing signal of the pressure sensing structure 1. The pressure sensing structure 1 and the signal processing chip 2 are respectively mounted on the substrate 4, and the substrate 4 and the rubber cover 3 are connected to each other, wherein the rubber cover 3 is provided therein with a mounting cavity 31. The substrate 4 covers the port of the mounting cavity 31 such that the pressure sensing structure 1 and the signal processing chip 2 are placed in the mounting cavity 31. The rubber cover 3 is provided with an opening 32 for sensing pressure, and the pressure is transferred to the pressure sensing structure 1 through the opening 32. The signal processing chip 2 includes an analog-digital conversion module 21, and the signal processing chip 2 is electrically connected to the substrate 4.

The rubber cover 3, as shown in FIG. 6, includes a base 33 and a boss 34 having an annular structure provided on the base 33. The boss 34 is provided with a first groove, a second groove is provided at the position of the base 33 corresponding to the first groove, wherein the first and the second grooves communicate with each other to form a mounting cavity 31. The pressure sensing structure 1 is mounted in the mounting cavity 31.

The signal processing chip 2 is mounted on the end face of the substrate 4 away from the rubber cover 3, as shown in FIG. 6. The pressure sensing structure 1 and the signal processing chip 2 are provided at different positions respectively so as to prevent the pressure sending structure 1 from squeezing the signal processing chip 2 under pressure, thereby protecting the signal processing chip 2.

In the embodiment of FIG. 6, the digital pressure sensor 100 further includes an epoxy resin 5 that covers an external surface of the signal processing chip 2 and a contact portion between the signal processing chip 2 and the substrate 4 so that the signal processing chip 2 is secured on the substrate 5. The epoxy resin 5 has good fluidity and low stress so that the substrate 4 and the signal processing chip 2 form as a whole, reducing external influences as well as improving anti-vibration and anti-impact performances and ensuring stability in use.

The above are only some embodiments of the present disclosure without limiting the present disclosure. Any modification(s), equivalent replacement(s) and improvement(s) made within principle of the present disclosure shall be considered within the scope of the present disclosure.

What is claimed is:

1. A digital pressure sensor, comprising:
a substrate;
a pressure sensing structure configured for measuring a pressure of an object to be measured;
a signal processing chip configured for receiving a sensing signal of the pressure sensing structure, the pressure sensing structure and the signal processing chip are mounted on the substrate, the signal processing chip has an analog-digital conversion module that converts the sensing signal output by the pressure sensing structure into a digital signal and outputs the digital signal, the signal processing chip is electrically connected to the substrate; and
a rubber cover having an opening through which the pressure is sensed, the substrate and the rubber cover are connected to each other and form a mounting cavity for holding the pressure sensing structure and the signal processing chip.

2. The digital pressure sensor of claim 1, wherein the pressure sensing structure has a soft rubber deformable under pressure and a pressure sensing chip configured for sensing deformation of the soft rubber and generating the sensing signal.

3. The digital pressure sensor of claim 2, wherein the pressure sensing chip is disposed on a side of the soft rubber away from the opening and is electrically connected to the substrate.

4. The digital pressure sensor of claim 2, wherein the soft rubber is a silica gel with which the mounting cavity is filled.

5. The digital pressure sensor of claim 2, wherein the signal processing chip is configured for sensing a temperature of the pressure sensing chip and implementing a temperature detection module that detects a temperature value of the object to be measured.

6. The digital pressure sensor of claim 2, further comprising a metal wire electrically connecting the pressure sensing chip and the substrate.

7. The digital pressure sensor of claim 1, wherein the rubber cover includes a base and a boss disposed on the base.

8. The digital pressure sensor of claim 7, wherein the boss has a first groove and the base has a second groove at a position corresponding to the first groove, the first groove and the second groove constitute the mounting cavity.

9. The digital pressure sensor of claim 8, wherein the pressure sensing structure is disposed within the mounting cavity.

10. The digital pressure sensor of claim 9, wherein the base has a second cavity configured for holding the signal processing chip, the second cavity and the mounting cavity are spaced apart.

11. The digital pressure sensor of claim 8, wherein the pressure sensing structure and the signal processing chip are stacked sequentially in the mounting cavity.

12. The digital pressure sensor of claim 9, wherein the signal processing chip is mounted on an end face of the substrate away from the rubber cover.

13. The digital pressure sensor of claim 12, further comprising an epoxy resin securing the signal processing chip on the substrate.

14. The digital pressure sensor of claim 13, wherein the epoxy resin covers an external surface of the signal processing chip and a contact portion between the signal processing chip and the substrate.

15. The digital pressure sensor of claim 1, further comprising an interaction device mounted on an outer surface of the rubber cover, the interaction device is electrically connected to the substrate.

16. The digital pressure sensor of claim 1, wherein the signal processing chip includes a data calibration module that compensates for the sensing signal.

* * * * *

UNITED STATES PATENT AND TRADEMARK OFFICE
CERTIFICATE OF CORRECTION

| | |
|---|---|
| PATENT NO. | : 11,536,623 B2 |
| APPLICATION NO. | : 17/085438 |
| DATED | : December 27, 2022 |
| INVENTOR(S) | : Yang Zhai et al. |

It is certified that error appears in the above-identified patent and that said Letters Patent is hereby corrected as shown below:

On the Title Page

Item [30] insert:
--October 30, 2019 (CN).......................201921851206.X--

Signed and Sealed this
Twentieth Day of June, 2023

Katherine Kelly Vidal
*Director of the United States Patent and Trademark Office*